US00PP12535P2

(12) United States Plant Patent
Vandenberg et al.

(10) Patent No.: US PP12,535 P2
(45) Date of Patent: Apr. 9, 2002

(54) CHRYSANTHEMUM PLANT NAMED 'YOCHESAPEAKE'

(75) Inventors: Cornelis P. Vandenberg, Salinas, CA (US); Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/774,371

(22) Filed: Feb. 1, 2001

(51) Int. Cl.[7] ..... A01H 5/00
(52) U.S. Cl. ..... Plt./295
(58) Field of Search ..... Plt./295

*Primary Examiner*—Bruce R. Campell
*Assistant Examiner*—Anne Marie Grünberg
(74) *Attorney, Agent, or Firm*—C. A. Whealy

(57) ABSTRACT

A distinct cultivar of Chrysanthemum plant named 'Yochesapeake', characterized by its upright and uniformly mounded plant habit; strong and vigorous growth habit; dark green foliage; uniform flowering response; suitability as either a disbud or natural spray-type; eight-week response time; freely flowering habit when grown as a natural spray-type; large daisy-type inflorescences that are about 7.4 cm in diameter when grown as a natural spray-type and about 10.3 cm in diameter when grown as a disbud-type; bright golden yellow ray florets; slow-maturing disc florets; and excellent postproduction longevity.

2 Drawing Sheets

BACKGROUND OF THE INVENTION

The present Invention relates to a new and distinct cultivar of Chrysanthemum plant, botanically known as *Chrysanthemum×morifolium* and hereinafter referred to by the name 'Yochesapeake'.

The new Chrysanthemum is a product of a planned breeding program conducted by the Inventors in Salinas, Calif. The objective of the breeding program is to create new potted Chrysanthemum cultivars that are suitable for year-round production with uniform plant growth habit, good vigor, desirable inflorescence form and floret colors, fast response time, and excellent postproduction longevity.

The new Chrysanthemum originated from a cross made by the Inventors in October, 1994, in Salinas, Calif., of the Chrysanthemum cultivar Sandusky, disclosed in U.S. Plant Pat. No. 9,369, as the female, or seed, parent with the Chrysanthemum cultivar Miramar, disclosed in U.S. Plant Pat. No. 7,469, as the male, or pollen, parent. The new Chrysanthemum was discovered and selected by the Inventors as a single flowering plant within the progeny of the stated cross grown in a controlled environment in Salinas, Calif. The selection of this plant was based on its uniform plant growth habit, good vigor, desirable inflorescence form and floret colors, fast response time, and excellent postproduction longevity.

Asexual reproduction of the new Chrysanthemum by vegetative tip cuttings was first conducted in Fort Myers, Fla. in June, 1997. Asexual reproduction by cuttings has shown that the unique features of this new Chrysanthemum are stable and reproduced true to type in successive generations.

SUMMARY OF THE INVENTION

The cultivar Yochesapeake has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Yochesapeake'. These characteristics in combination distinguish 'Yochesapeake' as a new and distinct Chrysanthemum:

1. Upright and uniformly mounded plant habit.
2. Strong and vigorous growth habit.
3. Dark green foliage.
4. Uniform flowering response.
5. Can be grown as either a disbud or natural spray-type.
6. Early flowering, eight-week response time.
7. Very freely flowering when grown as a natural spray-type.
8. Large daisy-type inflorescences that are about 7.4 cm in diameter when grown as a natural spray-type and about 10.3 cm in diameter when grown as a disbud-type.
9. Bright golden yellow ray florets and slow-maturing disc florets.
10. Excellent postproduction longevity with plants maintaining good substance and color for about three to four weeks in an interior environment.

Plants of the new Chrysanthemum can be compared to plants of the female parent, the cultivar Sandusky. In side-by-side comparisons conducted by the Inventors in Salinas, Calif., plants of the new Chrysanthemum differ from plants of the cultivar Sandusky in the following characteristics:

1. When grown as disbud-types, plants of the new Chrysanthemum have larger inflorescences than plants of the cultivar Sandusky.
2. Plants of the new Chrysanthemum have a more uniform spray formation than plants of the cultivar Sandusky.
3. Ray floret color of the new Chrysanthemum is bright golden yellow whereas ray floret color of the cultivar Sandusky is clear yellow.

Plants of the new Chrysanthemum can be compared to plants of the male parent, the cultivar Miramar. In side-by-side comparisons conducted by the Inventors in Salinas, Calif., plants of the new Chrysanthemum differ from plants of the cultivar Miramar in the following characteristics:

1. Inflorescences of the new Chrysanthemum appear to be fuller than inflorescences of the cultivar Miramar as ray florets of the new Chrysanthemum have short corolla tubes whereas ray florets of the cultivar Miramar have longer corolla tubes which give a gappy appearance to the inflorescences.

2. Plants of the new Chrysanthemum flower about one week earlier than plants of the cultivar Miramar.

3. Ray floret color of the new Chrysanthemum is bright golden yellow whereas ray floret color of the cultivar Miramar is clear yellow.

4. Inflorescences of the new Chrysanthemum produce little to no pollen whereas inflorescences of the cultivar Miramar produce abundant pollen.

Plants of the new Chrysanthemum can be compared to plants of the Chrysanthemum cultivar Yobutterfield, disclosed in U.S. Plant patent application Ser. No. 09/525,654. In side-by-side comparisons conducted by the Inventors in Salinas, Calif., plants of the new Chrysanthemum differ from plants of the cultivar Yobutterfield in the following characteristics:

1. Plants of the new Chrysanthemum have larger inflorescences than plants of the cultivar Yobutterfield.

2. Plants of the new Chrysanthemum can be grown as either disbud or natural spray-types whereas plants of the cultivar Yobutterfield are not suitable for production a disbud-type.

3. Ray floret color of the new Chrysanthemum is bright golden yellow whereas ray floret color of the cultivar Yobutterfield is clear yellow.

4. Plants of the new Chrysanthemum are more outwardly spreading than plants of the cultivar Yobutterfield.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which accurately describe the colors of the new Chrysanthemum.

The photograph at the top of the first sheet comprises a side perspective view of a typical flowering plant of 'Yochesapeake' grown as disbud-type.

The photograph at the bottom of the first sheet comprises a close-up view of typical inflorescences of 'Yochesapeake' grown as a disbud-type.

The photograph at the top of the second sheet comprises a side perspective view of a typical flowering plant of 'Yochesapeake' grown as natural spray-type.

The photograph at the bottom of the second sheet comprises a close-up view of typical inflorescences of 'Yochesapeake' grown as a natural spray-type.

DETAILED BOTANICAL DESCRIPTION

In the following description, color references are made to The Royal Horticultural Society Colour Chart except where general terms of ordinary dictionary significance are used. The following observations and measurements describe plants grown and flowered during the autumn in Salinas, Calif., in a fiberglass-covered greenhouse and under conditions which approximate those generally used in commercial potted Chrysanthemum production. During the production of these plants, the following conditions were measured: day temperatures, 21 to 27° C.; night temperatures, 17 to 19° C.; and light levels, 5,000 to 6,000 foot-candles. Four unrooted cuttings were directly stuck in 15-cm containers, exposed to long day/short night conditions, and pinched once about 14 days later. At that time, the photoinductive short day/long night treatments were started. Plants used for this description were grown as disbud and natural spray-types. Measurements and numerical values represent averages of typical flowering plants.

Botanical classification: *Chrysanthemum×morifolium* cultivar Yochesapeake.

Commercial classification: Daisy-type potted Chrysanthemum.

Parentage:

*Female, or seed, parent.*—*Chrysanthemum×morifolium* cultivar Sandusky, disclosed in U.S. Plant Pat. No. 9,369.

*Male, or pollen, parent.*—*Chrysanthemum×morifolium* cultivar Miramar, disclosed in U.S. Plant Pat. No. 7,469.

Propagation:

*Type.*—Terminal tip cuttings.

*Time to initiate roots.*—About four days at 21° C.

*Time to produce a rooted cutting.*—About ten days at 21° C.

*Root description.*—Fibrous and well-branched.

Plant description:

*Appearance.*—Herbaceous daisy-type potted Chrysanthemum which can be grown as a disbud or natural spray-type. Inverted triangle; stems mostly upright and somewhat outwardly spreading giving a uniformly mounded appearance to the plant. Freely branching, about four lateral branches develop after removal of terminal apex (pinching); dense and full plants. Vigorous.

*Plant height.*—About 28 cm.

*Plant width.*—About 42 cm.

*Lateral branches.*—Length: About 26 cm. Diameter: Thick, about 5 mm. Internode length: About 2.1 cm. Strength: Strong. Texture: Pubescent. Color: 144A.

*Foliage description.*—Arrangement: Alternate. Quantity of leaves per lateral stem: About 14. Length: About 5.9 cm. Width: About 5 cm. Apex: Rounded, cuspidate or emarginate. Base: Attenuate to truncate. Margin: Palmately lobed, sinuses between lateral lobes mostly convergent and overlapping. Texture: Upper and lower surfaces with very fine pubescence; veins prominent on lower surface. Color: Young foliage, upper surface: Darker than 147A. Young foliage, lower surface: Darker than 147B. Mature foliage, upper surface: 147A. Mature foliage, lower surface: 147B. Venation, both surfaces: 147B. Petiole length: About 1.6 cm. Petiole diameter: About 3 mm. Petiole color: 146B to 146C.

Inflorescence description:

*Appearance.*—Daisy-type inflorescence form with elongated oblong-shaped ray florets. Inflorescences borne on terminals above foliage. Disk and ray florets arranged acropetally on a capitulum. Not fragrant. Suitable for production as either disbud or natural spray-types.

*Flowering response.*—Under natural conditions, plants flower in the autumn/winter in the Northern Hemisphere. At other times of the year, inflorescence initiation and development can be induced under photoinductive short day/long night conditions (at least 13.5 hours of darkness). Early flowering; plants exposed to two weeks of long day/short night conditions followed by short day/long night conditions flower about 47 to 52 days later when grown as disbud-types and flower about 49 to 55 days later when grown as natural spray-types.

*Postproduction longevity.*—Inflorescences maintain good color and substance for about three to four weeks in an interior environment.

*Quantity of inflorescences.*—When grown as a natural spray-type, about nine inflorescences develop per lateral stem, or about 36 inflorescences per plant. When grown as a disbud-type, all the lateral inflorescences are removed leaving only the terminal inflorescence.

*Inflorescence bud.*—Height: About 6 mm. Diameter: About 1.1 cm. Color: Close to 143A.

*Inflorescence size, disbud.*—Diameter: Large, about 10.3 cm. Depth (height): About 2.1 cm. Diameter of disc: About 2.6 cm. Receptacle diameter: About 1.3 cm.

*Inflorescence size, natural spray.*—Diameter: About 7.4 cm. Depth (height): About 1.8 cm. Diameter of disc: About 1.9 cm. Receptacle diameter: About 8 mm.

*Ray florets.*—Shape: Elongated-oblong. Orientation: Initially upright, then about 90° from vertical or perpendicular to peduncle. Aspect: Initially concave, then mostly flat. Length: Disbud: About 5 cm. Natural spray: About 3.6 cm. Width: Disbud: About 1.3 cm. Natural spray: About 1.1 cm. Corolla tube length: About 4 mm. Apex: Acute, emarginate or dentate. Base: Attenuate; short corolla tube. Margin: Entire. Texture: Smooth, glabrous, satiny. Number of ray florets per inflorescence: About 35 arranged in about two rows. Color: When opening, upper and lower surfaces: 9A. Fully opened, upper surface: 9A, fading to 9B with subsequent development. Fully opened, lower surface: 9B.

*Disc florets.*—Arrangement: Massed at center of receptacle. Shape: Tubular, elongated. Apex: Five-pointed. Length: Disbud: About 9 mm. Natural spray: About 7 mm. Width: Disbud: Apex, about 2.5 mm; base, about 1 mm. Natural spray: Apex, about 2 mm; base, about 1 mm. Number of disc florets per inflorescence: Disbud: About 294. Natural spray: About 237. Color: Immature: 144A to 145A to 154A; development occurs slowly and green color is maintained. Mature: Apex: 9A. Mid-section: 154A. Base: 155A.

*Peduncles, natural spray.*—Length: First peduncle: About 5.6 cm. Fourth peduncle: About 7.5 cm. Seventh peduncle: About 10 cm. Diameter: About 3 mm. Angle to vertical: About 55° from vertical. Strength: Strong, flexible. Color: More green than 146A.

*Reproductive organs.*—Androecium: Present on disc florets only. Anther color: 9A to 12A. Pollen amount: Scarce to none. Pollen color: 12A to 15A. Gynoecium: Present on both ray and disc florets.

*Seed.*—Seed production has not been observed.

Disease resistance: Resistance to pathogens common to Chrysanthemums has not been observed on plants grown under commercial greenhouse conditions.

It is claimed:

1. A new and distinct cultivar of Chrysanthemum plant named 'Yochesapeake', as illustrated and described.

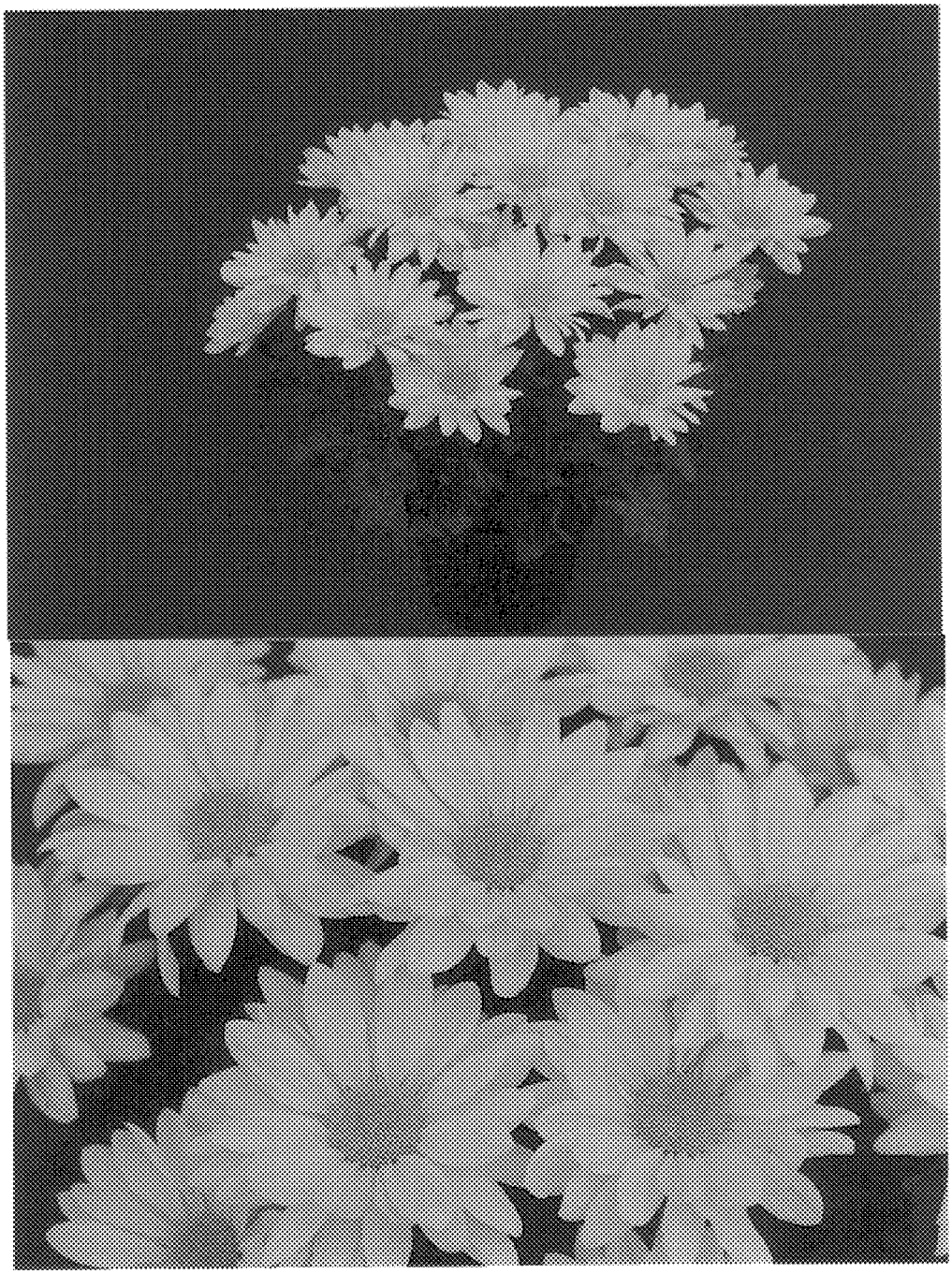

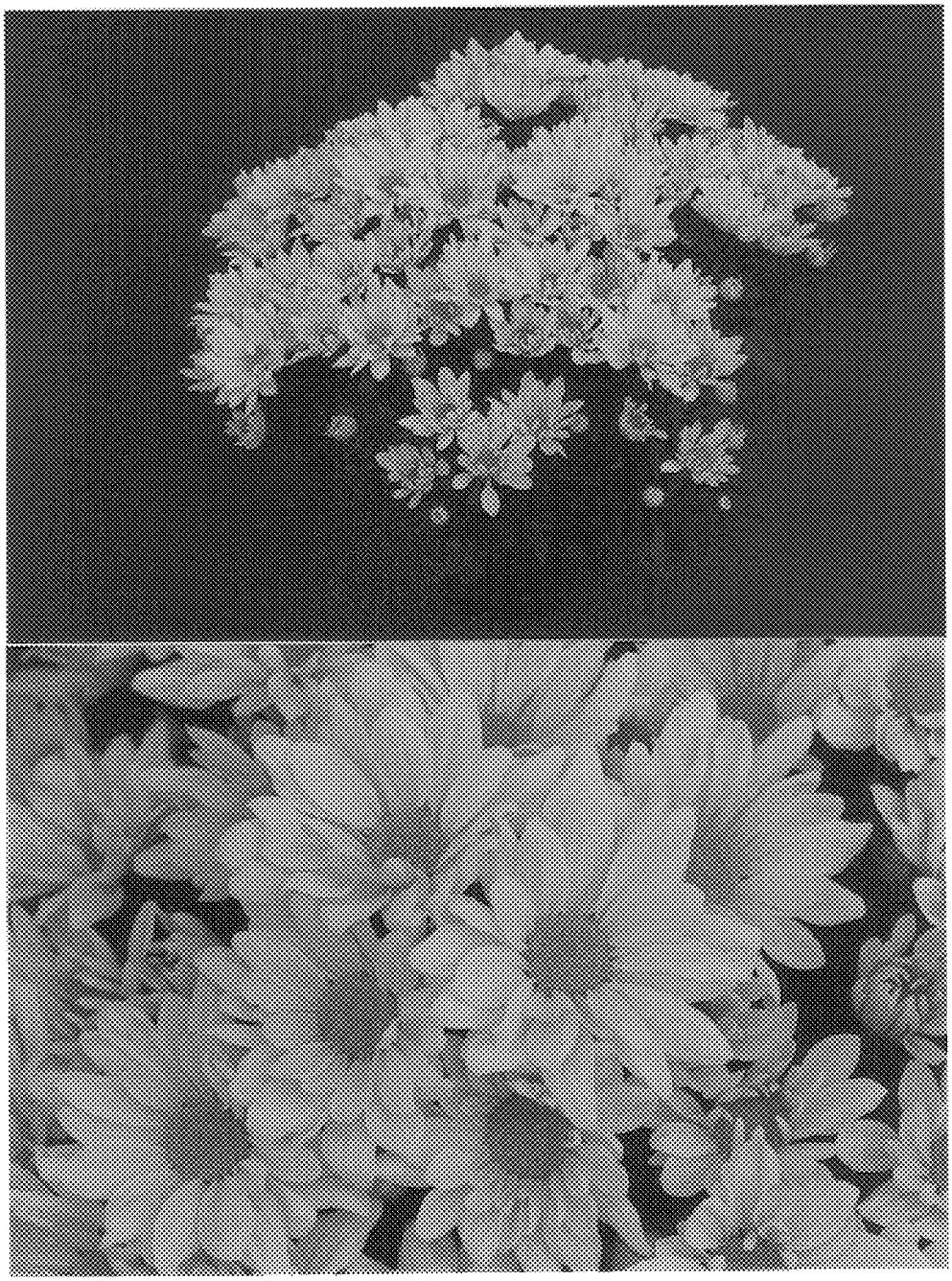

* * * * *